United States Patent [19]

Carlson

[11] 3,998,973
[45] Dec. 21, 1976

[54] THICKENING COMPOSITION

[75] Inventor: Bernard C. Carlson, Weston, Conn.

[73] Assignee: R. T. Vanderbilt Company, Inc., Norwalk, Conn.

[22] Filed: Apr. 7, 1975

[21] Appl. No.: 565,820

[52] U.S. Cl. .............................. 424/357; 106/262; 106/263; 252/8.5 A; 260/17 R; 260/29.6 MM; 260/42.55

[51] Int. Cl.² .......................................... A61K 7/48

[58] Field of Search ........... 424/357; 106/262, 263; 260/42.55, 29.6 S, 29.6 MM, 17 R; 252/8.5

[56] References Cited

UNITED STATES PATENTS

| | | | |
|---|---|---|---|
| 2,571,030 | 10/1951 | Gavett et al. .................. 424/68 X |
| 2,628,205 | 2/1953 | Shoemaker .................... 424/83 X |
| 2,914,443 | 11/1959 | Lynch ........................... 424/357 X |
| 2,996,432 | 8/1961 | Modderno ...................... 424/83 X |
| 3,019,161 | 1/1962 | Garai ........................... 424/357 X |
| 3,070,497 | 12/1962 | Knight ......................... 424/357 X |
| 3,100,174 | 8/1963 | Stevens ........................ 424/357 X |
| 3,196,079 | 7/1965 | Blaustein ...................... 424/83 X |
| 3,350,429 | 10/1967 | Hasegawa et al. .............. 260/583 |
| 3,450,666 | 6/1969 | Nease ............................. 260/40 |
| 3,574,827 | 4/1971 | Beerbower ...................... 424/83 |
| 3,636,200 | 1/1972 | Zentner ........................ 424/357 |
| 3,687,846 | 8/1972 | Lang .............................. 252/8.5 |
| 3,687,885 | 8/1972 | Abriss et al. ................. 260/29.6 |
| 3,708,435 | 1/1973 | Starkman ...................... 424/357 |
| 3,733,403 | 5/1973 | Chen ............................... 424/83 |
| 3,884,826 | 5/1975 | Phares, Jr. .................... 252/106 |

FOREIGN PATENTS OR APPLICATIONS

| | | |
|---|---|---|
| 1,474,022 | 2/1967 | France |
| 2,052,506 | 4/1972 | Germany |
| 780,918 | 8/1957 | United Kingdom ............... 424/83 |

*Primary Examiner*—Dale R. Ore
*Attorney, Agent, or Firm*—Brumbaugh, Graves, Donohue & Raymond

[57] ABSTRACT

The specification relates to a thickening composition containing a silicate, an ether or ester and a cellulose. The specification relates also to a process for thickening an aqueous organic system with this composition.

9 Claims, No Drawings

THICKENING COMPOSITION

BACKGROUND OF THE INVENTION

It is known to use finely divided, water-insoluble hydrous silicates as thickening and gelling agents for aqueous organic liquid preparations. These silicates are frequently available as colloidal clays of the montmorillonite and bentonite type.

Advantageously, the structure of the montmorillonite type clays is such that water and other polar molecules including certain organic molecules can enter between the unit layers of the lattice, thus causing the lattice to expand, i.e., a swelling effect occurs. The number of water layers readily absorbed between the structural layers of the montmorillonite depends on the type of lattice substitutions in the original structure. Possible substitutions include iron and lithium in place of aluminum in the octahedral sheet and aluminum to a limited extent for silicon in the tetrahedral sheet.

The net effect of thesesubstitutions is a negative charge on the structure which is always nearly of the same magnitude. This charge is balanced by cations held on the interlayer surfaces. These cations may be replaced with other suitable cations by appropriate treatment. The common exchangeable cations are Ca++, Na+, mg++ and H+. The type of exchangeable cation profoundly affects the physical properties of the mineral by influencing both the nature of the liquids held in the inter-layer space and the strength of the bonding force between the adjacent clay layers. Sodium bentonite which is described as a colloidal aluminum silicate containing montmorillonite has a similarly expandable structure.

These swellable or expandable clays normally hydrate in water. As a result of the hydration, a thickening effect is achieved upon dispersing the clay in the liquid system, especially under high shear conditions. Under low shear conditions, however, many types of colloidal clays are difficult to hydrate and surface active substances preferably are added to facilitate the process. Moreover, these thckeners are often high viscosity materials which are difficult to incorporate into viscous materials without at least initial dilution of the thickener or preferably, by addition of a surfactant.

In the past, therefore, a number of different types of polymers have been used for upgrading certain rheological and physical properties of clays and clay slurries for application as thickening agents in aqueous organic liquid systems. Thus, the viscosity of clay suspensions has been improved by adding polyethylene oxide to aqueous bentonite suspensions (Ger. Patent Publication No. 2,052,506) and by treating Western or natural sodium bentonite and subbentonite clays, i.e., calcium and magnesium variety of montmorillonite, with polymers containing carboxyl groups and higher polyethylene oxide (U.S. Pat. No. 3,687,846). The gel forming properties of montmorillonite clay have been improved by treatment with a complex of fatty amine and nonionic higher polymeric compound, such as polyoxyethylene lauryl ether and polyoxyethylene stearyl ether (U.S. Pat. No. 33,560,429). Other clay modifying polymers employed previously include polyoxyethylene fatty acid esters (U.S. Pat. No. 3,450,666). Furthermore, cellulosic thickeners, such as carboxymethylcellulose or its sodium salt, have been added to aqueous clay suspensions to improve such properties as viscosity, gel forming capacity, stability, ion exchange and salt compatibility (French Pat. No. 1,474,022).

Such modified clay systems have been used heretofore as thickening agents for various aqueous preparations and formulations. For instance, a paint thickening composition containing montmorillonite or benetonite, a nonionic surfactant of the polyoxyalkyl alcohol type and noncellulosic thickener is disclosed in U.S. Pat. No. 3,687,885 and a formulation of an ointment base with a mixture of clay and carboxymethylcellulose has been suggested [M.R. Baichwal et al., *Indian J. Pharm.*, 28 (11), 296-300, 1966].

It is also desirable to improve certain properties of a thhickening agent. Firstly, it may be preferable to utilize as little thickeneer as possible to achieve the required results. Secondly, the thickening agent should be resistant to floccing in aqueous systems containing electrolytes; that is, the colloidal structure of the thickening agent should be stable to electrolytes which may cause coagulation and separation from the system. These electrolyes occur commonly as necessary components in various preparations such as industrial emulsions, cosmetic creams and lotions, paint and similar formulations. Thirdly, it is advantageous to have no syneresis when the thickening agent is aged, for example, for 30 days.

SUMMARY OF THE INVENTION

It has now been discovered that such an improved thickening agent can be provided. Thus, in accordance with this invention, a synergistic composition is formed comprising colloidal magnesium aluminum silicate, a polyoxyethylene $C_{12-22}$ alkyl ether or ester and a sodium carboxymethylcellulose in the ratio of about 80:10:10 to 98:1:1, respectively. This composition in a 3% aqueous dispersion has a viscosity of about 100 to 5000 centipoises.

The composition of the invention can be employed as a thickening and gelling agent in a wide variety of aqueous organic liquid suspensions, emulsions and gels, and it improves the processing and applicational properties of such preparations and formulations. Furthermore, an aqueous solution of the synergistic thickening agent has excellent viscosity and flow properties, and it can be readily used in various aqueous organic solutions and dispersions.

DESCRIPTION OF THE INVENTION

The colloidal magnesium aluminum silicates are well known in theart as evidenced by U.S. Pat. No. 3,687,885 which is incorporated herein by reference. These hydrous silicates are available as purified clays of the swellable montmorillonite type. Preferably, the montmorillonites have a high magnesium content, and they possess the property of self-suspension, swelling and gelation in water. The montmorillonite clays are preferably finely divided and water insoluble to the extent that a 1% slurry provides a colloidal suspension. Silicates suitable for this invention, among others, are VEEGUM, VEEGUM T And VEEGUM HS (available from R. T. Vanderbilt Company, Inc.).

Another component in the thickening agent is a polyoxyethylene $C_{12-22}$ alkyl ether or ester, such as polyoxyethylene (20) cetyl ether, polyoxyethylene (20) stearyl ether, polyoxyethylene (23) lauryl ether, polyoxyethylene (50) monostearate, polyoxyethylene (20) monooleate, polyoxyethylene sorbitan monolaurate, polyoxyethylene sorbitan monopalmitate and polyoxyethylene sorbitan monooleate. These known ethers and esters are disclosed in art, such as U.S. Pat. Nos. 3,350,429, 3,687,885 and 3,450,666 which are incorporated herein by reference.

The thickening agent of the invention has a third component, namely, sodium carboxymethylcellulose. This compound is promulgated in French Pat. No. 1,747,022 which is incorporated herein by reference.

It is critical for this invention to have a high ratio of silicate to ether or ester to cellulose, that is, about 80:10:10 to 98:1:1, preferably about 84:8:8 to 96:2:2. A low ratio of silicate is unsatisfactory for the present invention.

The coating compositions may contain conventional optional additives, such as fillers, pigments, conventional stabilizers, curing agents, accelerators, foaming agents, catalysts, plasticizers, binders, flocculants, tackifiers, disperants, suspending agents and the like.

The manner in which the components are combined to form the synergistic thickening compositon of the present invention is generally not critical. Normally, simple dry mixing methods known in the art are satisfactory. It is also suitable to mix the components in situ, i.e., in the liquid desired to be thickened. Depending somewhat on the particular liquid composition to be formulated, low shear mixing methods are generally satisfactory. However, it is often advantageous to disperse the composition under high sheer conditions, such as roll mills, high speed blenders, ultrasonic mixers and the like. A preferred method of incorporating the synergistic thickener of the invention into aqueous organic liquid systems is as a preformed aqueous dispersion.

Liquid systems, which can be thickened by the thickening composition of the invention, are defined herewith as substances that under the specified dispersion conditions and prior to the addition of the thickening composition (1) flow continuously in response to shear stresses applied, (2) recover and (3) have a constant volume at a given temperature. Specific liquid systems include, among others, cosmetic and pharmaceutical preparations, such as cosmetic creams, lotions, soaps, hair treatment formulations and dentifrice preparations; and household product formulations, such as detergents, cleaning compositions, paint and paint removers. The thickening compositions of the invention can be used for controlling the viscosity of aqueous latexes of polymers of the natural and synthetic type, such as carboxylated styrene-butadiene synthetic rubber latex; polymers and copolymers of acrylonitrile with isoprene, butadiene or chloroprene; homopolymers of vinyl acetate and vinyl halide resins and copolymers of vinyl acetate and vinyl halide with ethylene, acrylic acid, acrylonitrile and vinylidene chloride; copolymers of styrene and unsaturated acid anhydrides; homopolymers and copolymers of acrylic and methaacrylic acid; ethylenically unsaturated monomers, such as styrene and other alkenyl aromatic monomers with butadiene and other open chain aliphatic conjugated dienes; acrylic monomers including alkyl acrylates, alkyl alkacrylates and chloroethylenic monomers; epoxy resins and other conventional aqueous film forming bases. The latexes may also be blends of emulsion polymerizates of two or more such latexes and may include oleoresinous film forming bases.

The amount of the thickening composition utilized in the liquid to be treated can vary greatly depending on such parameters as the type of liquid to be treated, extent of thickening desired, the degree of dispersion of the composition, the presence of additives and fillers. Taking into consideration the above conditions, the amount of thickening composition utilized can vary from about 0.1 percent to about 5.0 percent by weight of the liquid to be thickened.

Thus, in accordance with the invention, the combination of a colloidal magnesium aluminum silicate, a polyoxyethylene alkyl ether or ester and carboxymethylcellulose provides a thickening agent that is easy to hydrate and has improved gel structure. Synergistic thickening results in aqueous organic liquid systems are achieved by utilizing the thickening compositions of the invention, such as improved viscosity of the thickened preparations which remain stable upon aging, especially under low shear mixing conditions. In addition, other properties, such as salt compatibility, are improved. At the same time, the thickened system remains highly thixotropic, shows less tendency to produce syneresis, possesses good spreadability and color uniformity.

One of the criteria for acceptance of any coating composition is hiding power which is controlled to a large extent by the pigment volume concentration and by coating properties, i.e., the type of viscosity developed in the composition. By using thickening compositions of the invention, a type of viscosity can be developed without sacrificing hiding power and other coating characteristics, such as brush drage, flow and leveling properties of the coating. Moreover, inclusion of clay organic complexes in paints improves the dispersion of the pigment, impedes settling, controls viscosity and permits formulation that gives improved brushability and spraying.

The following examples are intended to illustrate but not to limit the invention. Unless otherwise indicated, all parts and percentages in the specification are claims are by weight.

EXAMPLE I

Compositions A, B, C and D were prepared with various ingredients indicated in Table 1. The thickening compositions therefrom were tested by determining Brookfield viscosity and salt compatibility as follows:

Brookfield Viscosity

Test solutions containing 3 percent solids are prepared by dry blending the components of the thickening agent and hydrating for 15 minutes in a Mixmaster under low shear conditions at 350 rpm. Brookfield viscosity of the test solutions is determined with Brookfiled LVT instrument using a single point spindle at 60 rpm and tabulated in Table 1 below.

Sat Compatibility

Salt compatibility is a measure of the resistance to floccing in sale media and is defined as the number of milliliters of 0.1 N NaCl required to floc 10 ml of 1 percent dispersion of the test material. The flocculation point is experimentally determined by preparing a series of 10 ml dispersions containing 1 percent of the test material, adding progressively 2, 4, 6, 8 or more milliliters of 0.1 N NaCl, adjusting the volume to 30 ml with distilled water and centrifuging. The flocculation point corresponds to the point of formation of an unstable gel as indicated by the separation of phases. The results of these tests are shown in Table 1.

It is evident from Table 1 that Composition A of the invention has a synergistic effect.

EXAMPLE II

The procedure of Example I was repeated using another silicate, with the exception that for the measurement of sale compatibility of compositions E and G, 0.5 N NaCl was used instead of 0.1 N NaCl. The ingredients and results are listed in Table 2.

Referring to Table 2, there is a synergism in composition E which is within the purview of the invention.

TABLE 1

| Ingredients | A | B | C | D |
| --- | --- | --- | --- | --- |
| Colloidal Magnesium Aluminum Silicate (a) | 90 | 100 | 90 | 90 |
| Polyoxyethylene (20) Stearyl Ether (b) | 5 | — | — | 10 |
| Sodium Carboxymethylcellulose (c) | 5 | — | 10 | — |
| Deionized Water | 3233 | 3233 | 3233 | 3233 |
| Total | 3333 | 3333 | 3333 | 3333 |
| Properties | | | | |
| Salt Compatibility ml 0.1 N NaCl | 8.0 | 3.5 | 6.0 | 3.0 |
| Brookfield Viscosity, cps. (3% solids) | | | | |
| Initial | 920 | 41 | 440 | 700 |
| After 1 day | 1120 | 135 | 880 | 980 |
| After 4 days | 1200 | 175 | 1000 | 1020 |
| After 7 days | 1240 | 210 | 1100 | 940 |

(a) VEEGUM T manufactured by the R. T. Vanderbilt Company, Inc.
(b) Brij 78 manufactured by the Imperial Chemical Ind.
(c) CMC 7MF manufactured by Hercules, Inc.

TABLE 2

| Ingredients | E | F | G | H |
| --- | --- | --- | --- | --- |
| Colloidal Magnesium Aluminum Silicate (a) | 90 | 90 | 90 | 100 |
| Polyoxyethylene (20) Stearyl Ether (b) | 5 | 10 | — | — |
| Sodium Carboxymethylcellulose (c) | 5 | — | 10 | — |
| Deionized Water | 3233 | 3233 | 3233 | 3233 |
| Total | 3333 | 3333 | 3333 | 3333 |
| Properties | | | | |
| Salt Compatibility ml 0.1 N NaCl | 40.0 | 5.0 | 30.0 | 3.5 |
| Brookfield Viscosity, cps. (3% solids) | | | | |
| Initial | 1200 | 260 | 580 | 8 |
| After 1 day | 1850 | 460(d) | 920 | 55 |
| After 4 days | 1750 | 740(e) | 1120 | 95 |
| After 7 days | 1700 | (e) | 1340 | 110 |

(a) VEEGUM manufactured by the R. T. Vanderbilt Company, Inc.
(b) Brij 78 manufactured by the Imperial Chemical Ind.
(c) CMC 7MF manufactured by Hercules, Inc.
(d) Some separation
(e) Separation

EXAMPLE III

Composition A of Example I and a control were incorporated into tempera paint formulations as indicated in Table 3 below:

TABLE 3

| Ingredients | Formulation 1(%) | Formulation 2(%) |
| --- | --- | --- |
| Composition A | 1.0 | — |
| Colloidal Magnesium Aluminum Silicate (a) | — | 1.5 |
| Propylene Glycol | 5.0 | 5.0 |
| Color | 1.0 | 1.0 |
| Titanium Dioxide | 1.0 | 1.0 |
| Water | 92.0 | 91.5 |

(a) VEEGUM T

After aging for 30 days, no syneresis was evident in Formulation 1 containing the thickening composition of the invention while formulation 2 had an edge of water, indicating syneresis.

EXAMPLE IV

As indicated in Table 4, moisturizing cream was formulated with the thickening composition E of Example 2 and compared with one formulated with silicate alone.

TABLE 4

| Ingredients | Formulation 3(%) | Formulation 4(%) |
| --- | --- | --- |
| Composition E | 1 | — |
| Colloidal Magnesium Aluminum Silicate (a) | — | 1.5 |
| Glycerin | 4.0 | 4.0 |
| Triethanolamine | 1.0 | 1.0 |
| Lanolin, Anhydrous (b) | 10.0 | 10.0 |
| Stearic Acid | 2.0 | 2.0 |
| Isopropyl Myristate | 2.0 | 2.0 |
| Glyceryl Monostearate SE | 3.0 | 3.0 |
| Cetyl Alcohol | 2.0 | 2.0 |
| Water | 75.0 | 74.5 |
| Brookfield Viscosity, cps. | | |
| Initial | 9600 | 5500 |
| 1 day | 9650 | 6200 |
| 7 day | 9700 | 6700 |
| 30 days | 9700 | 6900 |

(a) VEEGUM
(b) Lantrol manufactured by Malstrom Chemical Corporation.

The cream thickened with the composition of the invention offered considerably higher viscosity, easy hydration characteristics and good stability.

EXAMPLE V

Thickening composition I was prepared by blending 90 parts colloidal magnesium aluminum silicate (VEEGUM), 5 parts polyoxyethylene (20) cetyl ether (Brij 58) and 5 parts sodium carboxymethylcellulose. This composition was used to thicken an emulsifier-free cream. As a control, a second formulation was thickened with the colloidal magnesium aluminum silicate alone. The formulations and results are shown in Table 5.

TABLE 5

| Ingredients | Formulation 5(%) | Formulation 6(%) |
|---|---|---|
| Thickening Composition I | 3 | — |
| Collidal Magnesium Aluminum Silicate (a) | — | 5 |
| Propylene Glycol | 2 | 2 |
| Acetylated Lanolin (b) | 2 | 2 |
| Lanolin Derived Sterol Extract (c) | 6 | 6 |
| Petrolatum, White | 10 | 10 |
| Water | 77 | 75 |
| Brookfield Viscosity, cps. | | |
| Initial | 8500 | 4800 |
| 1 day | 9100 | 5400 |
| 7 days | 9100 | 6800 |

(a) VEEGUM
(b) Modulan manufactured by American Cholesterol Products, Inc.
(c) Amerchol L-101 manufactured by American Cholesterol Products Inc.

This example demonstrates that relatively a small amount of the synergistic thickening composition of the invention is effective in building viscosity in a water based formulation.

EXAMPLE VI

Composition J was prepared by dry blending and hydrating for three minutes in a Waring blender under high shear conditions with the ingredients listed in Table 6.

TABLE 6

| Ingredients | J (parts) |
|---|---|
| Colloidal Magnesium Aluminum Silicate (a) | 47.5 |
| Polyoxyethylene (20) Stearyl Ether (a) | 47.5 |
| Sodium Carboxymethylcellulose (a) | 5.0 |
| Deionized water | 3233.0 |
| & Total | 3333.0 |

(a) Same as Example I

Considerable foam was formed upon hydration of these ingredients. The Brookfield viscosity (3% solution) after 16 hours was 49 cps. Syneresis occurred after two days.

It is manifest from this example that a composition with a low amount of silicate is not suitable for this invention.

EXAMPLE VII

Thickening Composition K was prepared by blending 85 parts colloidal magnesium aluminum silicate, 5 parts polyoxyethylene (40) monostearate (TRYDET SA-40 manufactured by Trylon Chemical Division, Emery Industries) and 10 parts sodium carboxymethylcellulose (CMC 7H manufactured by Hercules, Inc.) under low shear conditions. This composition was used to thicken an acrylic latex paint. The thickened paint was tested by determining Brookfield viscosity with Brookfield LVT instrument using single point spindle at 10 rpm and calculating the thixotropic index (ratio of viscosity at 100 rpm to viscosity at 10 rpm). Stormer viscosity was determined by the ASTM Method D562-55. The paint formulation and results are shown in Table 7.

TABLE 7

| Ingredients | Pounds | Gallons |
|---|---|---|
| Thickening Composition K | & 7.0 | & 0.35 |
| Water | 435.2 | 52.24 |
| Hydroxyethyl Cellulose | 5.0 | 0.43 |
| Pigment Dispersing Agent (a) | 5.0 | 0.52 |
| Potassium Tripolyphosphate | 1.5 | 0.07 |
| Ethylene Glycol | 25.0 | 2.70 |
| Hexylene Glycol | 20.0 | 2.60 |
| Titanium Dioxide Pigment | 200.0 | 5.86 |
| Magnesium Silicate Pigment | 210.0 | 8.85 |
| Defoamer (b) | 4.0 | 0.53 |
| Preservative (c) | 1.1 | 0.15 |
| Acrylic Latex Emulsion (50%) | 225.0 | 25.57 |
| Ammonium Hydroxide (28%) | 1.0 | 0.13 |
| | 1139.8 | 100.00 |

| Aging Time | Brookfield Viscosity Cps. 10 RPM | Brookfield Viscosity Cps. 100 RPM | Thixotropic Index | Stormer Viscosity Kreb Unit (KU) |
|---|---|---|---|---|
| 1 Day | 10,520 | 1592 | 6.6 | 88 |
| 7 Days | 10,680 | 1600 | 6.7 | 87 |
| 4 Months | 10,720 | 1592 | 6.7 | 87 |

(a) DARVAN No. 7 manufactured by R. T. Vanderbilt Company, Inc.
(b) BALAB 747 manufactured by Witco Chemical Company
(c) VANCIDE TH manufactured by R. T. Vanderbilt Company, Inc.

Upon preparation of the paint formulation, the thickening comp9osition displayed good processing properties, particularly rapid hydration in water. As indicated by the above results, the paint had good thixotropic properties and retained its stability during storage.

Having set forth the general nature and specific embodiments of the present invention, the true scope is now particularly pointed out in the appended claims.

What is claimed is:

1. A thickening composition which comprises a synergistic misture of swellable colloidal magnesium aluminum silicate, a polyoxyethylene $C_{12-22}$ alkyl ether or ester having 20-50 oxyethylene units per molecule, and sodium carboxymethylcellulose in the ratio of about 80:10:10 to 98:1:1 by weight, respectively.

2. The composition according to claim 1 in which the polyoxyethylene compound is a polyoxyethylene $C_{12-22}$ alkyl ether having 20-50 oxyethylene units per molecule.

3. The composition according to claim 2 in which the polyoxyethylene alkyl ether is polyoxyethylene stearyl ether having 20–50 oxyethylene units per molecule.

4. The composition according to claim 2 in which the polyoxyethylene alkyl ether is polyoxyethylene cetyl ether having 20-50 oxyethylene units per molecule.

5. The composition according to claim 1 in which the colloidal magnesium aluminum silicate, polyoxyethylene compound and sodium carboxymethylcellulose are in the ratio of about 90:5:5 by weight, respectively.

6. A process for thickening an aqueous liquid selected from the group consisting of cosmetic preparation, household cleaning composition, paint and paint remover which comprises dispersing in the liquid between about 0.1 and 5.0 weight percent of a thickening compostion comprising a synergistic mixture of a swellable colloidal magnesium aluminum silicate, a polyoxyethylene $C_{12-22}$ alkyl ether or ester having 20–50 oxyethylene units per molecule, and sodium carboxymethylcellulose in the ratio of about 80:10:10 to 98:1:1 by weight, respectively.

7. The process according to claim 6 in which the liquid is a cosmetic preparation.

8. The process according to claim 6 in which the liquid is a household cleaning composition formulation.

9. The process according to claim 6 in which the liquid is a polymeric latex paint.

* * * * *

UNITED STATES PATENT OFFICE
CERTIFICATE OF CORRECTION

Patent No. 3,998,973          Dated December 21, 1976

Inventor(s) Bernard C. Carlson          Page 1 of 2

It is certified that error appears in the above-identified patent and that said Letters Patent are hereby corrected as shown below:

Col. 1, line 21, "thesesubstitutions" should read --these substitutions--;
Col. 1, line 28, "mg++" should be --Mg++--;
Col. 1, line 43, "thckeners" should be --thickeners--;
Col. 1, line 63, "33,560,429" should be --3,350,429--;
Col. 2, line 6, "benetonite" should be --bentonite--;
Col. 2, line 14, "thhickening" should be --thickening--;
Col. 2, line 15, "thickeneer" should be --thickener--;
Col. 2, line 50, "theart" should read --the art--;
Col. 2, line 60, "And" should be --and--;
Col. 3, line 8, "1,747,022" should be --1,474,002--;
Col. 3, line 57, "methaacrylic" should be --methacrylic-
Col. 4, line 29, "drage" should be --drag--;
Col. 4, line 37, "are" should be --and--;
Col. 4, line 53, "Brookfiled" should be --Brookfield--;
Col. 4, line 56, "Sat Compatibility" should be --Salt Compatibility--;

UNITED STATES PATENT OFFICE
CERTIFICATE OF CORRECTION

Patent No. 3,998,973      Dated December 21, 1976

Inventor(s)    Bernard C. Carlson      Page 2 of 2

It is certified that error appears in the above-identified patent and that said Letters Patent are hereby corrected as shown below:

Col. 4, line 58, "sale" should be --salt--;
    Col. 5, line 7, "sale" should be --salt--;
    Col. 4-5, Examples I & II, throughout Examples I & II "N NaCl" should read --N NaCl--;
    Col. 7, line 42, delete "&" before --Total--;
    Col. 7, line 65, after "rpm" insert --and 100 rpm--;
    Col. 7, line 66, "(ratio of viscosity at 100 rpm to viscosity at 10 rpm" should be --(ratio of viscosity at 10 rpm to viscosity at 100 rpm)--;
    Col. 8, line 4, delete "&" before --7.0-- and --0.35--;
    Col. 8, line 24, "comp9osition" should be --composition--
    Col. 8, line 33, "misture" should be --mixture--.

Signed and Sealed this

Tenth Day of May 1977

[SEAL]

Attest:

RUTH C. MASON
Attesting Officer

C. MARSHALL DANN
Commissioner of Patents and Trademarks